United States Patent [19]

Pfohl

[11] Patent Number: 4,981,139
[45] Date of Patent: Jan. 1, 1991

[54] VITAL SIGNS MONITORING AND COMMUNICATION SYSTEM

[76] Inventor: Robert L. Pfohl, 485 S. Paseo Bandera, Anaheim Hills, Calif. 92807

[21] Appl. No.: 232,897

[22] Filed: Aug. 16, 1988

Related U.S. Application Data

[63] Continuation-in-part of Ser. No. 920,238, Oct. 17, 1986, abandoned, which is a continuation-in-part of Ser. No. 522,640, Aug. 11, 1983, Pat. No. 4,619,268, and a continuation-in-part of Ser. No. 827,777, Feb. 7, 1986, Pat. No. 4,705,048, which is a continuation of Ser. No. 660,454, Oct. 12, 1984, abandoned.

[51] Int. Cl.$^5$ .......................................... A61B 5/0205
[52] U.S. Cl. .................................... 128/671; 128/715; 128/736; 128/773
[58] Field of Search .............. 128/670, 671, 700, 715, 128/736, 773, 903, 904, 908, 680, 687, 689, 709, 774; 250/338.1

[56] References Cited

U.S. PATENT DOCUMENTS

| | | | |
|---|---|---|---|
| 2,729,211 | 1/1956 | Peter | 128/2.1 |
| 3,182,129 | 5/1965 | Clark et al. | 179/1 |
| 3,405,288 | 10/1968 | Dittrich | 310/8.4 |
| 3,488,586 | 1/1970 | Watrous et al. | 324/96 |
| 4,129,125 | 12/1978 | Lester et al. | 128/2.05 R |
| 4,141,350 | 2/1979 | Shinoda | 128/2.05 S |
| 4,176,660 | 12/1979 | Mylrea et al. | 128/671 |
| 4,184,485 | 1/1980 | Agoston | 128/670 |
| 4,237,900 | 12/1980 | Schulman et al. | 128/630 |
| 4,248,241 | 2/1981 | Tacchi | 128/671 |
| 4,301,809 | 11/1981 | Pinchak | 128/695 |
| 4,304,239 | 12/1981 | Perlin | 128/642 |
| 4,304,240 | 12/1981 | Perlin | 128/671 |
| 4,306,567 | 12/1981 | Krasner | 128/671 |
| 4,308,870 | 1/1982 | Arkans | 128/640 |
| 4,312,358 | 1/1982 | Barney | 128/670 |
| 4,331,156 | 5/1982 | Apple et al. | 128/688 |
| 4,349,031 | 9/1982 | Perlin | 128/642 |
| 4,362,164 | 12/1982 | Little et al. | 128/639 |
| 4,362,166 | 12/1982 | Furler et al. | 128/670 |
| 4,369,794 | 1/1983 | Furler | 128/671 |
| 4,383,534 | 5/1983 | Peters | 128/671 |
| 4,475,555 | 10/1984 | Linder | 128/670 |
| 4,479,494 | 10/1984 | McEwen | 128/682 |
| 4,484,583 | 11/1984 | Graham | 128/671 |
| 4,510,943 | 4/1985 | Miyamae | 128/680 |
| 4,580,575 | 4/1986 | Birnbaum et al. | 128/671 |
| 4,633,498 | 12/1986 | Warnke et al. | 381/23.1 |
| 4,651,746 | 3/1987 | Wall | 128/671 |
| 4,657,025 | 4/1987 | Orlando | 128/671 |
| 4,803,625 | 2/1989 | Fu et al. | 128/908 |
| 4,827,943 | 9/1989 | Bornn et al. | 128/903 |

FOREIGN PATENT DOCUMENTS

| | | | |
|---|---|---|---|
| 0009295 | 4/1980 | European Pat. Off. | 128/903 |
| 2823931 | 12/1979 | Fed. Rep. of Germany | 455/606 |

OTHER PUBLICATIONS

Groeneveld, "Infra-Red Controlled Command Receiver For Implantable Telemetry", Med. & Bio. Eng. & Comput. 1983 vol. 21 pp. 227-228.

"Esophageal Lead for Intraoperative Electro cardiographic Monitoring", by Robert A. Kates et al., 9-1982, pp. 781-785.

"Conjunctival Oxygen Monitoring System" (Orange Medical Instruments Orange I), 12 pages of A Technical Summary.

"Oesophageal Probe for Heart and Temperature Monitoring during Angesthesia", by D. Linnarsson et al., 5-1982, pp. 389-392.

*Primary Examiner*—Ruth S. Smith
*Attorney, Agent, or Firm*—Baker, Maxham, Jester & Meador

[57] ABSTRACT

A system for monitoring the vital signs of a patient includes a plurality of sensing units for sensing a plurality of physiologic conditions of a patient connected to a microprocessor that is responsive to the sensing units for providing an alarm signal in response to a deviation of a condition to an alarm state from a predetermined norm, a voice enunciating alarm responsive to an alarm signal for generating a voice sound identifying the physiological condition reaching an alarm state, an infrared transmitter having an omni-directional antenna for transmitting certain vital sign sounds and the voice sound, and a portable infrared receiver for receiving and producing the vital sign sounds and the voice sound for enabling untethered remote monitoring of the physiological conditions.

18 Claims, 4 Drawing Sheets

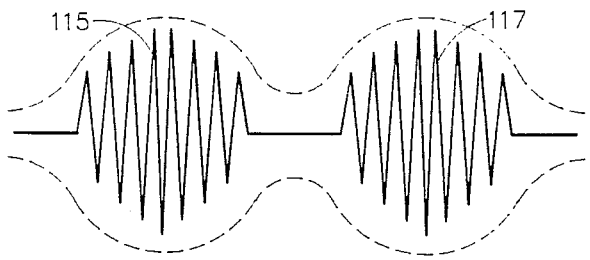
FIG. 4
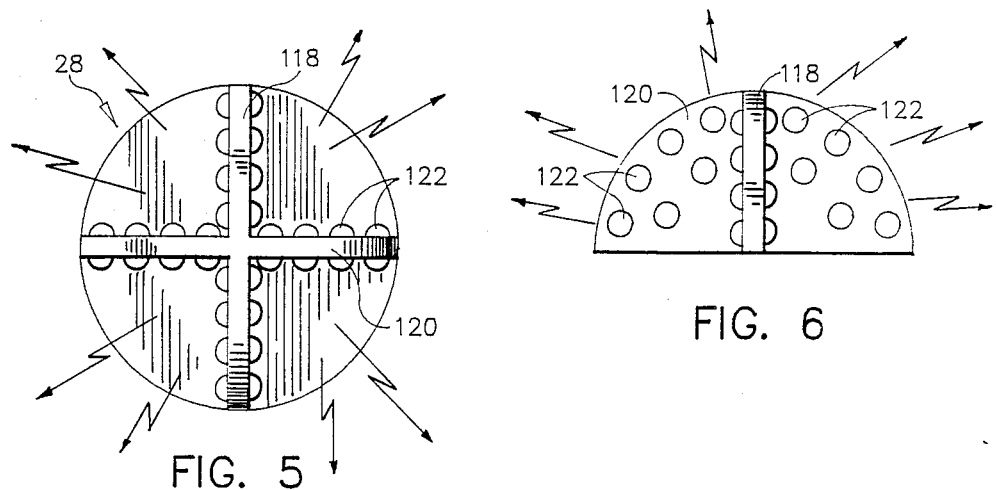
FIG. 5
FIG. 6
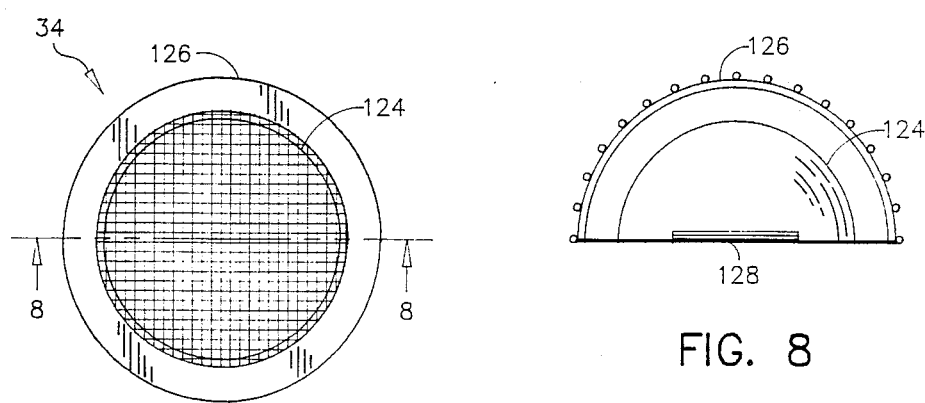
FIG. 7
FIG. 8

VITAL SIGNS MONITORING AND COMMUNICATION SYSTEM

REFERENCE TO RELATED APPLICATIONS

This application is a continuation-in-part of U.S. patent application entitled "Vital Signals Monitoring and Communication System", Ser. No. 920,238, filed Oct. 17, 1986, now abandoned inventor: Robert L. Pfohl; which is a continuation-in-part of Ser. No. 522,640, filed Aug. 11, 1983, now U.S. Pat. No. 4,619,268, inventors: James D. Uphold and Robert L. Pfohl; and of "Vital Signals Monitoring System", Ser. No. 827,777, filed Feb. 7, 1986, now U.S. Pat. No. 4,705,048, inventor: Robert L. Pfohl, which is a continuation of Ser. No. 660,454, filed Oct. 12, 1984 of the same title, now abandoned.

BACKGROUND OF THE INVENTION

The present invention relates to patient vital signs monitoring systems and pertains particularly to an improved multi-mode portable system with a wireless communication system for operating room environments.

In the first aforementioned application, of which I am co-inventor, a vital signs monitoring system is disclosed which includes a number of physiologic condition monitoring sensors, including an esophageal stethoscope incorporating a miniature microphone for pick up and transmission of signals representative of the sounds generated within the chest of a patient. These sounds of particular interest include the breathing sounds and the heart sounds. Processing circuits enable separation of the breath and heart sounds, as desired by the operator. These circuits also enable measurement of heart or pulse and breath or respiration rates, and comparison of these measured rates with preset reference rates. The system is also provided with means for initiating a visual or audible alarm in response to critical variations from the norm. The system further includes temperature sensing means in the esophageal catheter and a processing system for processing the various signals.

A wireless communication link comprises an omnidirectional IR transmitter and a portable receiver. The transmitter transmits the vital signs sounds by way of IR waves to a miniature portable receiver carried by a monitoring physician or anesthesiologist. This system frees the anesthesiologist from the usual tube and wire constraints and permits maximum mobility with full monitoring capability during and following medical procedures.

During the critical times prior to and subsequent to insertion of the esophageal stethoscope into the patient, vital signs are normally monitored by an air tube stethoscope, which monitors the heart and breath sounds or the blood flow sounds during measurement of blood pressure. This procedure, however, unduly ties the anesthesiologist to the patient during this critical monitoring period, or in the alternative leaves the patient unmonitored during brief moments when the anesthesiologist must attend to other matters within an operating room.

In my prior U.S. Patents, I disclose systems for solving many of these problems. Subsequent improvements, as covered herein, have been developed to enhance the reliability of those systems, as well as add numerous useful monitoring functions.

Another problem, to which the present invention is directed, is that of the interference from other electrical and electronic equipment in the hospital operating room, such as electrosurgical equipment. Such equipment generate and emit or transmit large amounts of electromagnetic energy that overwhelm and interfere with any electronic transmission systems within the vicinity. Attempts to use AM an FM radio signals in the hospital operating and high intensity care rooms have not been successful. Initial attempts by the inventor to use the IR system resulted in difficulties due to interference from other electronic equipment.

Still another problem with monitoring equipment in operating rooms is in the vast number of monitoring systems and the noise and alarms associated therewith. The sounding of an alarm requires the monitoring physician to identify or locate the alarm, identify the problem vital sign and determine the problem. This is time consuming, under even optimum conditions, and is particularly confusing under multiple alarm conditions.

It is, therefore, desirable that a vital signs monitoring system be available, which permits a monitoring physician to constantly reliably monitor the vital signs of a patient, with full freedom to move about an operating room.

The present system provides means for overcoming these and other problems of prior systems.

SUMMARY AND OBJECTS OF THE INVENTION

It is the primary object of the present invention to provide an improved vital signs monitoring system for a living being.

In accordance with the primary aspect of the present invention, a vital signs monitoring system includes a plurality of electronic sensors for selectively and continuously sensing various vital signs indicative of physiologic conditions, including heart and breathing sounds, blood pressure, blood flow sounds, various temperatures, and other parameters. These sensors are connected to a central processing control system for selectively processing the various sensed signals, sending the sensed signals by way of a wireless communication system to a monitoring physician. The communication system includes an omni-directional IR transmitter communicating with a miniature IR receiver to enable a monitoring physician to selectively monitor the respective sounds. A voice synthesizer responds to an alarm signal and pinpoints the problem vital sign parameter.

Another aspect of the invention includes the combination of a system, which includes an esophageal stethoscope, with a sound and temperature processing system wherein the processing system is keyed to a norm for the vital signs, and activates an alarm system in response to deviation from normal signs. A selector switching arrangement enables the monitoring physician to select a selected one of the chest or blood pressure sounds sensor or the esophageal sensor.

BRIEF DESCRIPTION OF THE DRAWINGS

The above and other objects and advantages of the present invention will become apparent from the following description when read in conjunction with the drawings wherein:

FIG. 4 is an illustration of waves being monitored;

FIG. 5 is a top plan view of the transmitter antenna;

FIG. 6 is a side elevation view of the transmitter antenna of FIG. 5;

FIG. 7 is a top plan view of the receiver antenna; and

FIG. 8 is a section view taken on line 8—8 of FIG. 7.

DETAILED DESCRIPTION OF A PREFERRED EMBODIMENT

Figure 1:
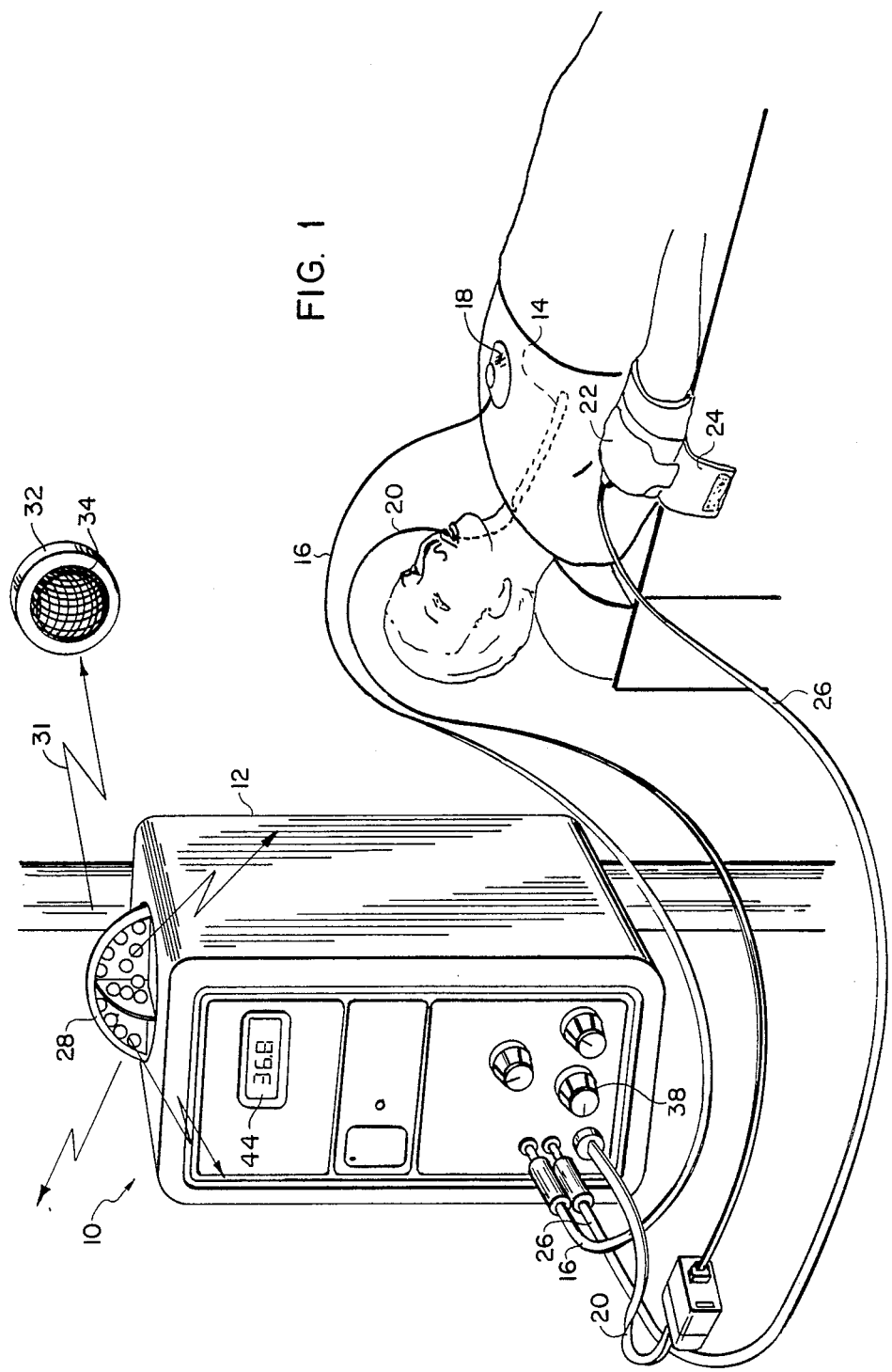
FIG. 1 is a perspective view illustrating a preferred embodiment of the system in position and connected to a patient for monitoring.

Referring to the drawings and particularly to FIG. 1, a monitoring system in accordance with the invention is illustrated as applied to a patient. The monitoring system comprises a monitoring unit, designated generally by the numeral 10, which comprises a housing 12 which will hereinafter be referred to as the control unit in which is housed a main monitoring and control system, including a microprocessor unit, basic electronics for the system, various display and alarm devices, and a wireless infrared (IR) transmitter as will be described. A number of sensing devices or instruments are connected to the monitoring system.

The illustrated sensing devices or instruments comprise first an electronic esophageal stethoscope 14, connected by electrical leads 20 to the main monitoring or control unit 12. An electronic precordial chest sounds sensor 18 is mounted on the patient's chest and is connected by electrical lead 16 to the control unit 12. An electronic blood pressure sounds sensor 22 is mounted over the brachial artery of the patient and secured in place under a blood pressure cuff 24, shown partially open in FIG. 1, and is connected by electrical leads 26 to the control unit 12. The sound sensor 18 and 22 are of the type more fully illustrated and described in my U.S. Pat. No. 4,705,048, granted Nov. 10 1987, which is incorporated herein by reference as though fully set forth.

The esophageal catheter 14 comprises an elongated pliable tube or sheath covering for encapsulating the end of a lead cable, which contains or houses the leads to a microphone and a thermistor, positioned at the closed or distal end of the sheath, for protectively covering by the sheath. The probe is constructed of the usual material for such probes and is of a convenient size for insertion into the esophagus. The lead 20 is of sufficient length to extend to and couple to the appropriate monitoring equipment.

Figure 2:
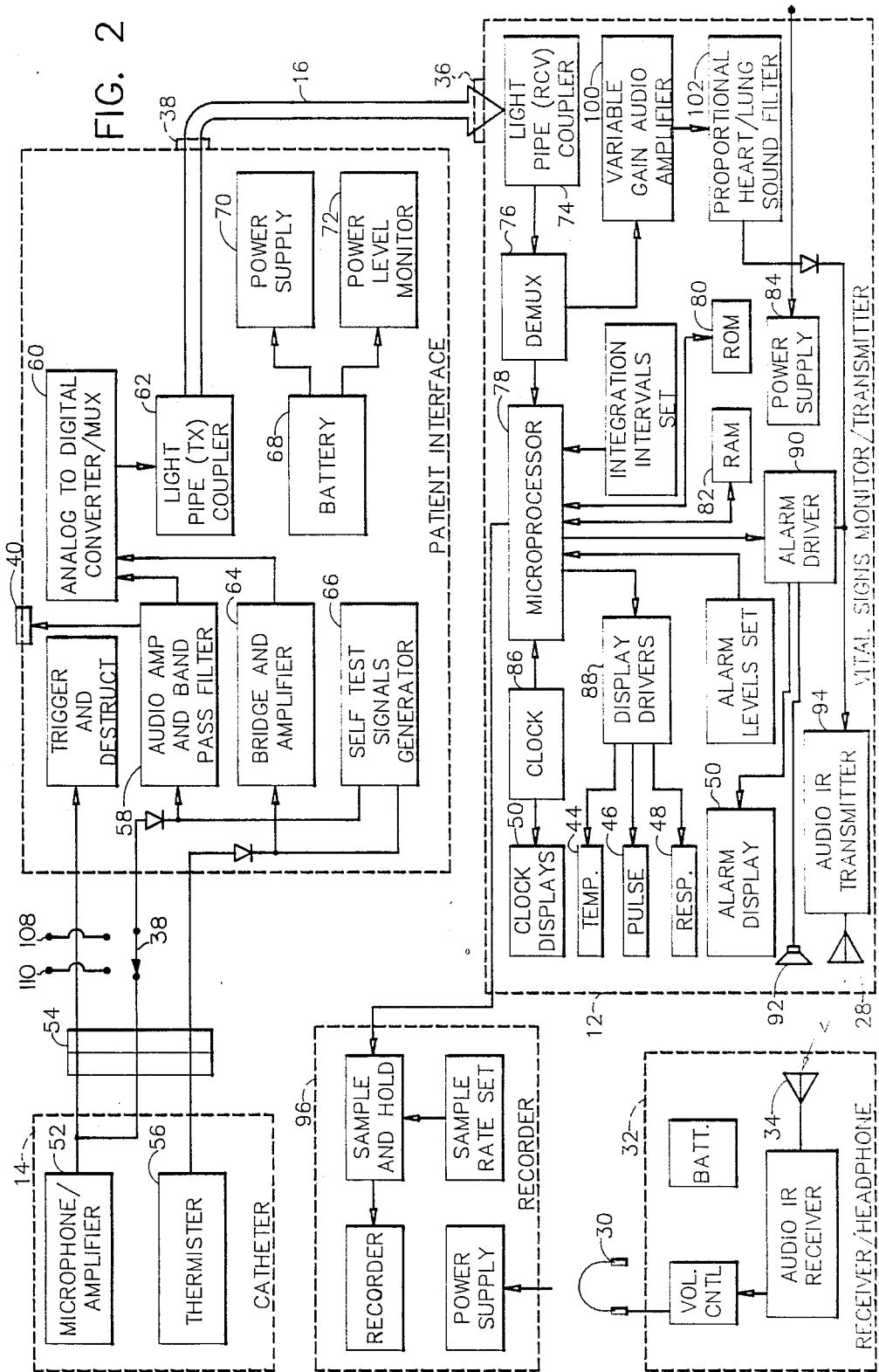
FIG. 2 is a functional block diagram for the embodiment of FIG. 1.

The control unit 12 includes various signal processing and indicating systems and includes a wireless IR transmission system, including an infrared transmitter with an omni-directional infrared antenna 28, which transmits an IR signal 31 throughout a room to be received by a miniature portable receiver 32, carried by a monitoring physician, and monitored by means of a suitable earphone or the like. In this embodiment, a temperature display 44 only has been provided, although others as illustrated in FIG. 2 may be provided if desired.

Certain sounds may be selected by a suitable switch arrangement 38 to an audio IR transmitter, (see also FIG. 2) which transmits a signal 31 to a portable audio IR receiver 32 carried by a monitoring physician with a suitable earphone or the like for monitoring the sounds. This basic system is covered in more detail in the aforementioned patent, which is incorporated herein by reference.

The system, as illustrated in FIG. 1 also includes several precordial sensing instruments, as above mentioned, to enable monitoring of the patient's vital signs before the esophageal stethoscope 14 is inserted and connected, and during any interruption in the monitoring through the esophageal sensor, as well as subsequent to removal of the esophageal tube sensor system.

The sounds picked up by the precordial sensors or microphones 18 and 22 are transmitted in the form of electrical pulses from the microphones and are processed through one or more filters (not shown), in FIG. 1 such as bandpass filters like filter 58 (FIG. 2) for filtering out background noises and the like. The inputs shown in FIG. 2, would be input to filter 58 with input to converter 60. The signals are also processed through a suitable amplifier and automatic gain control 100 and proportional filter 102 to further enhance the signals. The signals are then selectively transmitted by the audio IR transmitter to the physician by way of the portable IR receiver 32 having an IR receiver antenna or eye 34, and an ear piece 30. A selector switch array 38, (FIGS. 1 and 3), enables the physician to selectively monitor the precordial chest sensor, the blood pressure sounds sensor or the esophageal stethoscope.

The microprocessor is also programmed to monitor these heart sounds by assigning a to a standard sound for a given patient and comparing subsequent sounds (e.g., FIG. 4) to the standard. For example, transducers are sensitive to frequency, amplitude and duration and generate signals that are a quantitative representation of these. These signals are typically analog, but can be converted to digital for better microprocessor handling. The microprocessor can detect trends in these sounds and generate an alarm signal, should the sounds indicate that the heart has reached an alarm (i.e. critical) state.

A temperature sensing device or unit, such as a thermistor, is also preferably carried by the sensing unit 22 and engages the surface of the skin for sensing the external temperature of the patient. The signals from the thermistor are transmitted by suitable electrical conductors, to the processing system for processing in the usual fashion, for comparison and display as desired.

The sounds picked up by the microphone in sensor unit 22 are transmitted by suitable electrical leads through the cord 26 to the processing and control unit, wherein the signals are filtered through a filter system or circuit, such as a bandpass filter or the like, and thereafter amplified and controlled through automatic gain control unit before being transmitted by way of the switch array, and the audio IR transmitter to the monitoring physician by way of his miniature portable receiver 32.

The monitor system, in accordance with the invention, includes four main sub-assemblies comprising a catheter assembly, a patient interface unit, monitor/transmitter unit, and a receiver/ear piece assembly. The patient interface unit (FIG. 2) comprises a low powered analog signal processing circuitry with a standard analog to digital signal converter and a battery power supply. The battery power supply preferably includes alternate rechargeable batteries. The signal output from the analog to digital converter is converted into light signal format by means of a conventional fiberoptic coupler 62, and transmitted by a fiberoptic cable 61 to the monitor/transmitter unit. Thus, the patient is entirely electrically isolated from either ground or line power electrical potential by means of this mechanization.

The monitor/transmitter unit includes a conventional microprocessor, a special infrared transmitter, circuitry for electrical interfacing with the patient interface unit, and the system control panel. The control panel contains the basic functional controls for controlling the various functions and operations of the system to be more fully described later.

Turning to FIG. 2 of the drawing, wherein like numbers will indicate like components, a functional block diagram illustration of the functional elements and relationship of the system, as disclosed in the parent application, now U.S. Pat. No. 4,619,268, is illustrated. The system comprises a basic electronic vital signs monitor with a basic control system 12, which houses the basic signal and data processing components with the various sensors being interfaced with the control system unit by means of suitable plug-in cords or cables such as 16, 20 and 26 (FIG. 1).

The catheter 14 includes a microphone and preamp circuit 52 connected through suitable leads through a connector 54, which connects into the patient interface unit. The microphone 52 is adapted to pick up and transmit signals representative of any sounds, such as heart and breathing and other sounds within the body. These signals are passed through amplifier and filter 58, and are available for direct monitoring at socket 40. Also, the signals representing heart and breathing sounds are further monitored by CPU 78 and passed through a filtering circuit 102 to the audio IR transmitter 94, as will be explained.

Temperature response means, such as a thermistor 56, is also disposed within the catheter and connected by suitable electric leads to the connector 54.

The esophageal stethoscope 14, as disclosed in my U.S. Pat. No. 4,619,268, granted Oct. 28, 1986, and fully incorporated herein by reference, also includes temperature sensing means and a series of filters and amplifiers 58 in the processing unit 12, (FIG. 2), which filter and enhance the signals sensed, and processes the data through a processing system, which includes a microprocessing unit or CPU 78, including ROM memory 80 and RAM memory 82, and the appropriate software programming to monitor the vital functions through the esophageal and other sensors. The CPU 78 is programmed to activate the appropriate display or displays 44, 46, 48 and alarms 51, as shown in FIG. 2, and not provided for in FIG. 1.

Referring to the patient interface unit, (FIG. 2), signals from the microphone 52 are transmitted to an audio amplifier and bandpass filter 58 for filtering and selecting the desired sounds, such as heart beat and breathing, and are then transmitted to the analog to digital converter multiplexer 60, which converts the signals to digital format, and then transmits the signal to a light pipe coupler 62 for transmission by way of the optical fiber or light pipe 61 to the monitor/transmitter unit.

The signal from the thermistor or temperature sensing element 56 is transmitted by suitable electrical conductors, through an electrical bridge circuit and amplifier 64, and then to the analog to digital converter multiplexer 60 for transmission via the light coupler and light pipe 16 to the monitor/transmitter unit 12. A self-test signal generator 66 is connected to the circuit for testing the patient interface unit by simulating microphone and thermistor signals. Unit power comes from a suitable battery, such as a nine volt transistor battery 68, coupled to a power supply 70, and includes a power level monitor 72. Monitoring of the battery power is important in order to insure adequate power for operation of the system.

The signals from the patient interface unit are communicated by means of the fiberoptic cable 61 to the light pipe or optical coupler 74, from which it is transmitted to a demultiplexer 76, and then transmitted to the microprocessor unit 78. The microprocessor unit may be any suitable microprocessor chip set. The preferred microprocessor unit is such as that available from the Intel Corporation as a number 8085. This is a four MHz clock rate device.

The microprocessor unit is programmed to control and compute the many functions for the system. The microprocessor unit 78 is intercoupled to suitable memory devices, such as a ROM memory chip 80 and a RAM memory chip 82. The microprocessor is programmed, as will be more fully explained, for monitoring the many parameters and carrying out the functions set forth herein.

A power supply 84 is connected to a suitable source of power, such as a battery or other source. The microprocessor 78 is programmed to first carry out a test of the hardware of the system, and after the system is confirmed to be operational, it monitors and processes the data received from the sensing units, and compares the data to reference data either pre-programmed or self-programmed from prior monitoring and activates a suitable alarm system should critical limits be exceeded.

A clock 86, preferably a quartz crystal oscillator, is interfaced with the microprocessor 78, and functions to supply accurate time and elapsed time to the microprocessor unit and to drive clock displays on the LCD 50. The microprocessor functions to control display drivers 88, which function to drive the displays 44, 46 and 48 for temperature, pulse and respiration rates display indicators. The microprocessor also drives alarm driver 90 for driving the display alarm through the LCD 50, and audible alarms through the audible alarm speaker 92. Similarly, the alarm driver transmits the alarm signals through an audio infrared (IR) transmitter 94, which transmits the signal to the audio receiver unit 32.

A recorder 96 may be connected into the system for receiving and recording signals and data from the microprocessor. Various recorders may be suitable for this purpose and preferably would include a power supply, a paper or magnetic tape recorder, with a sample and hold buffer, with a sample rate set function programmed in.

The monitor/transmitter unit also includes a variable gain auto audio amplifier 100 receiving a signal from the demultiplexer 76, which is fed through a proportional heart-lung sound filter 102 for separating the heart and lung sounds and transmitting them to the audio IR transmitter 94.

The controls of the monitoring system include means for setting the time intervals during which the microprocessor monitors each input. Similarly, the microprocessor can be programmed to set alarm levels for the various functions.

Figure 3:
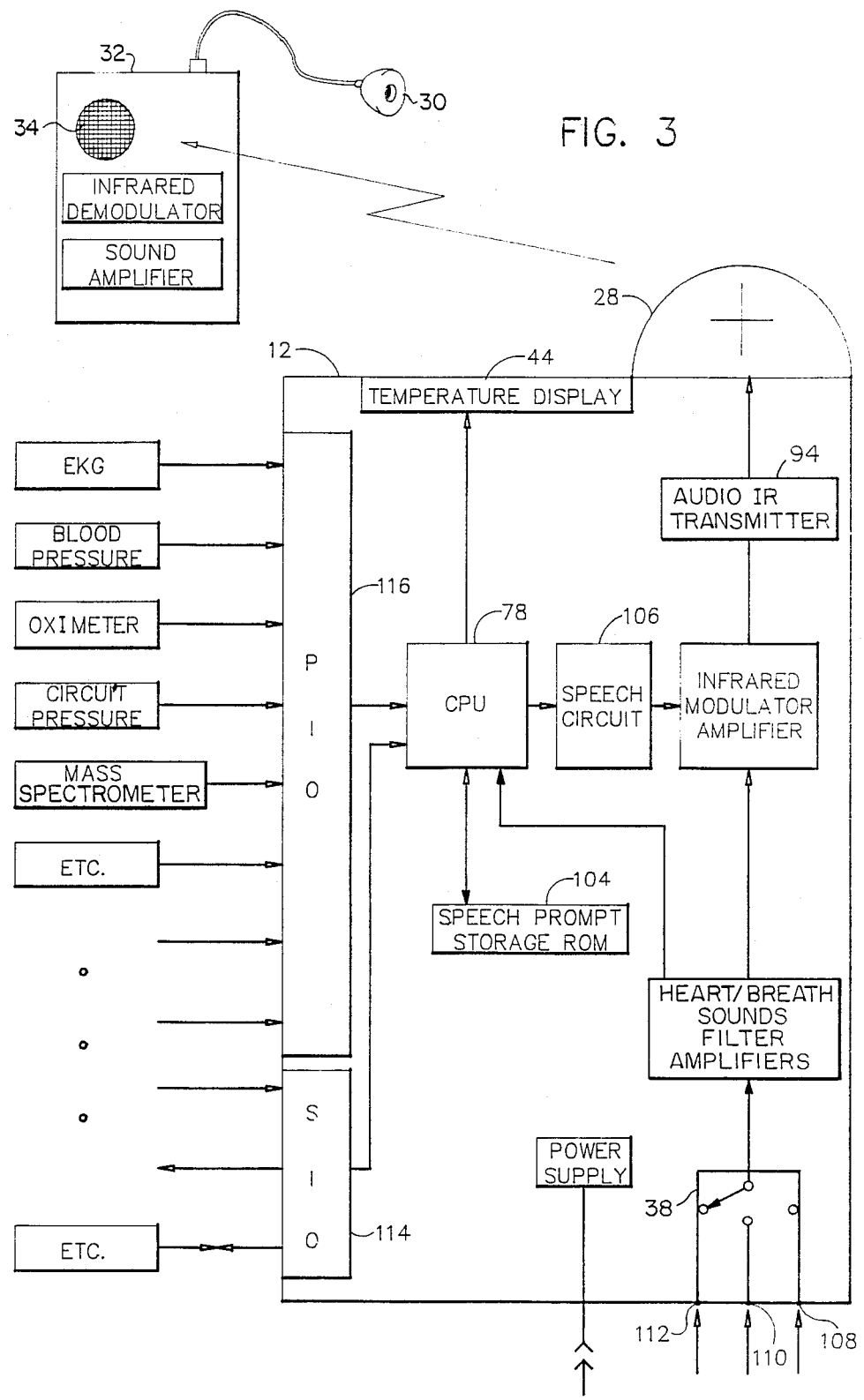
FIG. 3 is a functional block diagram showing another embodiment of the invention.

Referring to FIG. 3, an alternate embodiment is illustrated wherein the system, in accordance with the invention, has been modified to include speech synthesis means responsive to alarm signals to identify a vital sign which has reached alarm conditions. The speech system, as illustrated, includes a speech prompt storage ROM 104 and a speech circuit 106, such as an OKI MS 5205 connected to the microprocessor 78. The ROM chip 104 is programmed to include digital representation of the appropriate words and is accessed by the microprocessor 78. The CPU 78 is programmed so that an alarm condition of a vital sign prompts it to select the appropriate data from ROM 104, and transmits that data to the speech synthesis chip 106. The chip or circuit 106 responds and generates an electrical signal that represents a voice identification of that sign, e.g. "heart", "temperature", "lungs", "breathing", etc. This signal is transmitted via the audio transmitter to the receiver and is heard by the monitoring operator or physician as a voice. This voice immediately draws the operators attention to the appropriate monitor and reduces delay in focusing on the problem area.

In the case of multiple alarms, the system is programmed to give priority to the most serious condition. For example, certain alarm conditions of the heart may be considered more critical to the life of the patient than certain alarm conditions of the lungs. The CPU is simply programmed so that if, for example, a heart signal and a lung signal reaches alarm state at the same time, the CPU will respond to the heart signal prior to responding to the lung signal. Also if the heart signal reaches alarm state after the lung signal, but before the CPU has had time to respond, (i.e. initiate a voice prompt), it will respond first to the heart signal.

The system includes input cable connectors 108, 110, and 112 for sound inputs from the esophageal stethoscope, the precordial stethoscope, and the blood pressure acoustic input respectively. These sounds are processed and selected ones selected by selector 38 are transmitted to the operator via the IR transmitter. These may also be monitored for initiation of the voice alarm system.

An RS 232 serial intput/output (SIO) port 114 is provided for connecting other monitors or the like to the microprocessor 78. Alarms from other external and/or independent monitors can be connected into the system to prompt the voice circuit to voice the alarm to the operator via the IR transmitter. The system is preferably programmed to enable the voice alarm to override any other sounds being transmitted to the receiver. The voice alarm may be directed through the system microphone or through the receiver ear piece or both.

An additional bank of cable input connectors or plugs 116 such as parallel input/output port or connector (PIO) is also connected to the microprocessor for the input of alarms from other monitoring equipment. Numerous stand alone monitors for various physiological conditions have been developed in recent years. The present system is designed to interface with these monitors to provide the most comprehensive data to the monitoring physician. These monitors include EKG, blood pressure, oximeter, circuit pressure, mass spectrometer. The term "circuit pressure" refers to respiratory circuit. These can be monitored by the system from data input or by responding to alarms or alarm signals from these monitors.

The system is also programmed to monitor and recognize trends in a condition that may not be perceptible to the operator. For example, certain blood flow sounds can indicate the condition of the heart. Changes in these sounds that are normally not detectable by the human ear can indicate a change in the condition of the heart. These sounds can be monitored by the microprocessor by measuring these sounds, for example, as to duration and amplitude, as illustrated in FIG. 4, so that minute changes not detectable to the human ear may be detected by the microprocessor. In the same manner, changes in other parameters can be more closely monitored by the system.

The communications link of the system utilizes an infrared wave system, rather than the traditional radio wave communication system. The traditional radio wave communication system, even that approved for medical use, has been found to be impractical in the hospital surgical and emergency room environment. Much of the equipment in the hospital produces electromagnetic waves that interfere with radio wave communication systems. This equipment also interferes with other wireless systems, including the infrared.

The present system has been developed to provide an efficient communication link and avoid interference from electromagnetic energy generated by hospital equipment. The system utilizes infrared light waves as the carrier signal for the sound transmission system. The infrared light waves are in the range from 770 to $10 \times 6$ nanometers (nm). This falls within the region between the longest of the visible spectrum and the shortest of the microwaves. These waves can be made to fill a room without interfering with electronic equipment, and are room confined so that they will not interfere with an IR system in an adjacent room. Moreover, a hospital can be equipped with several IR communication systems utilizing the same frequency without interference. Thus, any receiver can function with any of the systems.

The present system comprises an IR transmitter having an omni-directional antenna for transmitting the waves outward in all directions from the central point of the antenna. The IR waves reflect off the walls of the room and thus fill the room. The receiver can then be located anywhere within the room. The antenna, as illustrated in FIGS. 5 and 6, comprises a support structure having a plurality of infrared light emitting diodes mounted and positioned on the support structure, so that light emitted from the diodes radiate outward in at least a partially spherical (semi-spherical) direction from a center point of the antenna structure. The illustrated embodiment comprises a generally semi-spherical dome shaped structure, having walls 118 and 120 dividing it into quarter segments. The walls of the segments are covered with a plurality of IR emitting diodes 122 positioned so that IR is radiated outward in all directions from a central point of the antenna. Each wall of diodes of the antenna covers a different segment of the circle and portion of the sphere. The support structure can also take the form of a spherical surface on which the diodes are mounted.

The IR receiver is a semi-spherical lens 124, having a radio wave shield 126 disposed thereover. These, cover a light cell 128 or electro-optical receiving device, such as an electro-optic diode which responds to the light waves received for generating signals that are processed in the receiver for reproducing the transmitted sounds. The shield 126 is constructed of a wire mesh having a wire diameter of about 0.007 inches, and a mesh opening is about $0.018 \times 0.024$ inches. An open mesh copper wire fabric of about the above dimensions has been found to shield against electromagnetic interferences from other hospital equipment in emergency and operating rooms. The shield 126 will allow IR waves to pass through, but will block electromagnetic waves in the radio wave frequency band.

The receiver unit includes an infrared demodulator and sound amplifier for converting the waves back to an audible sound. The sound is then communicated to the operator through his earphones.

The system is programmed, as described in the aforementioned U.S. Pat. No. 4,619,268 to automatically enter into a test mode for testing the various components of the system, then go into a set limits mode to permit the limits of the various functions to be set, and thereafter go into the monitoring mode for monitoring the physiological conditions, such as heart rate, breath rate and body temperature, and compare these values with reference or alarm set limit values. Critical deviations from the reference rates signal the microprocessor to drive a suitable audio or visual alarm.

In operation, the unit is powered on, the various self-test mode routine is initiated, and the various components functions are checked. During the self-test mode, the testing of the system progresses with displays of mode test conditions, etc., being displayed by the display 50. A switch activates the system to go into the operational monitoring mode after the systems have been checked and determined to be functional.

The audio control includes a balance control with knob 39, (FIG. 1), for selecting either heart or breath rate, or both, as would be selected as desired. Volume control with knob 41 permits adjustment of the audio volume for the audio signal indicator, which may be a beeper, buzzer, horn or the like. An alarm off control is preferably provided and permits temporary disconnect of the alarm from the system. A temperature alarm control permits setting of the temperature or alarm limit with a Centigrade/Fahrenheit selector control for selecting the temperature scale.

If limits are not programmed in for the parameters, the system will default to normal parameter, e.g. 37.0 degrees Centigrade (or 98.6 degrees Fahrenheit), 70 beats/min., 17 breaths/min. A complete system, as disclosed herein, is readied in an operating room or preparatory room with the components thereof, including the esophageal stethoscope, an electronic precordial chest sensor unit and an electronic blood pressure Korotkoff sounds sensor unit. The electronic precordial chest sensor and the electronic blood pressure sounds sensor unit may be attached immediately to the patient, and connected to the vital signs monitor and control unit. The unit may be turned on and blood pressure and chest sounds immediately monitored selectively prior to the insertion of the electronic esophageal stethoscope. The attending physician merely mounts the IR radio receiver, which in the preferred embodiment comprises a unit approximating the size of a cigarette pack, with volume control and an earphone attached. The physician simply places the receiver unit in a pocket or clips it to his coat and inserts the ear plug or ear piece in his ear for listening. The physician may then selectively monitor either one of the chest sounds or the blood pressure sounds during the period prior to insertion of the esophageal stethoscope.

Typically, anesthetic is administered prior to the insertion of the esophageal stethoscope, thus creating a critical monitoring period. After the esophageal stethoscope is inserted and attached to the vital signs monitoring and control unit, the stethoscope may be selected for monitoring by the physician. The internal chest and heart sounds, as well as internal temperature, are then monitored with the physician in constant receipt of the sounds of the heart and breath of the patient.

At any time during the procedure, the physician may selectively switch to either the monitoring or sensor units for monitoring the various sounds, as well as monitoring the internal and external temperature through the temperature sensing elements. Differences between internal and external temperature can be easily and quickly monitored, which also gives the physician an indication of the condition of the patient. He may also monitor the output from the many external monitors as previously described.

The present system is described in sufficient detail to enable one of ordinary skill in the relevant art to practice the invention. Many of the separate components, which are not described in detail herein, are state of art. For example, suitable microprocessing units are available from Intel Corporation as an 8085, and equivalent units are available from National Semiconductor Corporation.

The above described system provides an elaborate system of simple and effective components that enables a physician, such as an anesthesiologist, to monitor the condition of a patient from a period prior to the administering of anesthesia, and prior to the insertion of the esophageal stethoscope and the like, during and administering of anesthesiology, during surgery, and subsequent to surgery. The system also gives the monitoring physician complete freedom to move about an operating room, without being tethered to the patient's monitoring system by means of conventional air column tubes as in the prior art devices.

While I have illustrated and described my invention by means of a specific embodiment, it is to be understood that numerous changes and modifications may be made therein without departing from the spirit and scope of the invention as defined in the appended claims.

I claim:

1. A patient vital signs monitoring system comprising:
   sensing means for sensing a plurality of physiological conditions of a patient and generating a monitoring signal indicative of each of said physiological conditions;
   alarm means responsive to each of said monitoring signals for providing an alarm signal in response to a deviation of a physiological condition to an alarm state from a predetermined norm;
   voice enunciating means responsive to said alarm signal from said monitoring means for generating a voice sound identifying the physiological condition reaching an alarm state;
   infrared transmitter means having omni-directional antenna means for transmitting said voice sound; and
   portable infrared receiver means for receiving and reproducing said voice sound for enabling remote monitoring of said physiological conditions.

2. The monitoring system of claim 1 wherein:
   one of said conditions is temperature; and
   said means responsive to each of said monitoring signals includes programmable means for establishing a reference temperature, and temperature alarm means for providing an alarm signal in response to a critical deviation of the temperature sensed from said reference temperature.

3. The monitoring system of claim 1 wherein:
   one of said conditions is the condition of the heart; and
   said means responsive to each of said monitoring signals includes means for monitoring the condition of the heart by monitoring the sounds of the heart.

4. The monitoring system of claim 3 wherein:
said means responsive to each of said monitoring signals includes programmable means for establishing a reference heart sound, and heart sound alarm means for providing an alarm signal in response to a deviation in said heart sound from said reference heart sound.

5. The monitoring system of claim 1 wherein:
one of said conditions is the condition of breathing; and
said means responsive to each of said monitoring signal includes means for monitoring the condition of breathing by monitoring breathing sounds, programmable means for establishing a reference breathing sound, and breathing sound alarm means for providing an alarm signal in response to a critical deviation of said breathing sound from said reference sound.

6. A patient vital signals monitoring system comprising:
sensing means for sensing a plurality of physiological conditions of a patient and for generating a monitoring signal representative of each of said physiological conditions;
monitoring means responsive to said monitoring signals for providing an alarm signal in response to a deviation of a physiological condition to an alarm state from a predetermined norm;
voice enunciating means responsive to an alarm signal for generating a voice sound identifying the physiological condition reaching an alarm state;
infrared transmitter means having omni-directional antenna means for transmitting said voice sound; and
portable infrared receiver means for receiving and reproducing said voice sound for enabling remote monitoring of said physiological conditions, said portable infrared receiver for receiving said IR waves includes an electro-optic diode and radio wave shielding means for shielding said diode from radio waves.

7. The monitoring system of claim 6 wherein:
one of said conditions is temperature; and
said monitoring means includes programmable means for establishing a reference temperature, and temperature alarm means for providing an alarm signal in response to a critical deviation of the temperature sensed from said reference temperature.

8. The monitoring system of claim 6 wherein:
one of said conditions is the condition of the heart; and
said monitoring means includes means for monitoring the condition of the heart by monitoring the sounds of the heart.

9. The monitoring system of claim 6 wherein:
said monitoring means includes programmable means for establishing a reference heart sound, and
heart sound alarm means for providing an alarm signal in response to a deviation in said heart sound from said reference heart sound.

10. The monitoring system of claim 6 wherein:
one of said conditions is the condition of breathing; and
said monitoring means includes means for monitoring the condition of breathing by monitoring breathing sounds, programmable means of establishing a reference breathing sound and breathing sound alarm means for providing an alarm signal in response to a critical deviation of said breathing sound from said reference breathing sound.

11. The monitoring system of claim 6 comprising:,
multiple input means for input to said means responsive to said monitoring signals of monitoring signals selected from the group consisting of EKG, blood pressure, oximeter, circuit pressure, and mass spectrometer.

12. The monitoring system of claim 6 wherein:
said infrared transmitter omni-directional antenna means comprises a support having a generally semi-spherical configuration;
a plurality of infrared emitting diodes mounted and positioned on said support for directing IR waves outward in at least a semi-spherical direction from a center point of said support.

13. The monitoring system of claim 12 wherein:
said radio wave shielding means comprises a fine mesh wire screen.

14. A patient vital signs monitoring system comprising:
sensing means for sensing a plurality of physiologic conditions of a patient;
monitoring means responsive to said sensing means for monitoring and providing an alarm, signal in response to a deviation of physiological condition to an alarm state from a predetermined norm;
voice enunciating means responsive to said alarm signal for generating a voice sound identifying the physiological condition reaching an alarm state;
one of said conditions is temperature, said monitoring means including programmable means for establishing a reference temperature, and temperature alarm means for providing an alarm signal in response to a critical deviation of the temperature sensed from said reference temperature;
one of said conditions is the condition of the heart, said monitoring means including means for monitoring the condition of the heart by monitoring the sounds of the heart, programmable means for establishing a reference heart sound, and heart sound alarm means for providing an alarm signal in response to a deviation in said heart sound from said reference heart sound;
one of said conditions is the condition of breathing, said monitoring including means for monitoring the condition of breathing by monitoring breathing sounds, programmable means for establishing a reference breathing sound, and alarm means for providing an alarm signal in response to a critical deviation of said breathing sound from said reference breathing sound;
multiple input means for inputting monitoring signals selected from the group consisting of EKG, blood pressure, oximeter, circuit pressure, mass spectrometer to said monitoring means;
infrared transmitter means having omni-directional antenna means for transmitting said voice sound, said infrared transmitter omni-directional antenna means comprises support means for forming a generally semi-spherical configuration;
a plurality of infrared emitting diodes mounted and positioned on said support means for directing IR waves outward in at least a semi-spherical direction from a center point of said support means; and
a portable infrared receiver for receiving said IR waves includes an electro-optic diode and radio wave shielding means for shielding said diode.

15. The monitoring system of claim 14 wherein: said radio wave shielding means comprises a fine mesh wire screen.

16. The monitoring system of claim 15 wherein said monitoring means includes programmable means for establishing upper and lower limits for each of the parameters of temperature, heart rate, and breath rate.

17. A patient vital signs monitoring system comprising:

monitoring means for monitoring a plurality of physiological conditions;

an elongated flexible esophageal catheter having a closed distal end and a proximal end and having detachable connecting means on said proximal end for connecting said catheter to said monitoring means;

sound responsive means in said distal end of said catheter for generating sound signals in response to sound waves;

amplifying means in said catheter for amplifying said sound signals;

temperature responsive means in said catheter for generating a signal indicative of a temperature;

signal processing means for receiving said sound signals and separating said sound signals for determining patient heart and respiration rate and comparing said rates to a predetermined reference rate;

sound alarm means responsive to a predetermined critical difference between said compared rates for generating an alarm signal;

temperature signal processing means for comparing said temperature signal to a predetermined reference signal;

temperature alarm means responsive to a critical difference between said temperature signal and said reference signal for generating a temperature alarm signal;

voice enunciating means responsive to any one of said alarm signals for generating a voice identification of the parameter generating said alarm signal;

said monitoring means receiving and monitoring said signals and including an infrared transmitter having an omni-directional antenna for transmitting said heart sound signals and said breathing sound signals and said voice identification;

a portable infrared receiver for receiving and reproducing said sound signals for enabling remote monitoring of said heart beat sounds and said breathing sounds;

said omni-directional antenna comprises support means having a generally semi-spherical configuration;

a plurality of infrared emitting diodes mounted and positioned on said support means for directing IR waves outward in at least a semi-spherical direction from a center point of said support means; and said portable infrared receiver for receiving said IR waves includes an electro-optic diode and ratio wave shielding means for shielding said diode.

18. A patient vital signs monitoring system comprising:

monitoring means for monitoring a plurality of physiological conditions;

an elongated flexible esophageal catheter having a closed distal end and a proximal end and having detachable connecting means on said proximal end for connecting to said monitoring means;

sound responsive means in said distal end of said catheter for generating sound signals in response to sound waves;

amplifying means in said catheter for amplifying said sound signals;

temperature responsive means in said catheter for generating a signal indicative of a temperature;

signal processing means for receiving said sound signals and separating said sound signals for determining patient heart and respiration rate and comparing said rates to a predetermined reference rate;

sound alarm means responsive to a predetermined critical difference between said compared rates for generating an alarm signal;

temperature signal processing means for comparing said temperature signal to a predetermined reference signal;

temperature alarm means responsive to a critical difference between said temperature signal and said reference signal for generating a temperature alarm signal;

input means for input of alarm signals from external monitoring means taken from the group consisting of EKG, blood pressure, oximeter, circuit pressure, mass spectrometer;

voice enunciating means responsive to any one of said alarm signals for generating a voice identification of the parameter generating said alarm signal;

said monitoring means receiving and monitoring said signals, and including an infrared transmitter having an omni-directional antenna for transmitting said heart sound signals, said breathing sound signals and said voice identification, said antenna comprises support means having a generally semi-spherical configuration, a plurality of infrared emitting diodes mounted and positioned on said support structure for directing IR waves outward in at least a semi-spherical direction from a center point of said support means; and a portable infrared receiver for receiving said IR waves comprising an electro-optic sensor shielded by radio wave shielding means for receiving and reproducing said sound signals for enabling remote monitoring of said heart beat sounds and said breathing sounds.

* * * * *